United States Patent [19]

Rothfuss

[11] 4,345,600

[45] Aug. 24, 1982

[54] PURSE-STRINGER

[75] Inventor: Robert G. Rothfuss, Bellevue, Ky.

[73] Assignee: Senco Products, Inc., Cincinnati, Ohio

[21] Appl. No.: 174,813

[22] Filed: Aug. 4, 1980

[51] Int. Cl.$^3$ ............................................. A61B 17/04
[52] U.S. Cl. ................................. 128/334 R; 128/346
[58] Field of Search ............... 128/346, 334 R, 334 C, 128/335, 321, 322, 340; 223/109 R; 112/227

[56] References Cited

U.S. PATENT DOCUMENTS

| | | | |
|---|---|---|---|
| 755,921 | 3/1904 | O'Neill | 128/334 R |
| 1,982,207 | 11/1934 | Furniss | 128/346 |
| 3,247,852 | 4/1966 | Schneider | 128/346 |
| 3,323,208 | 6/1967 | Hurley | 30/124 |
| 3,349,772 | 10/1967 | Rygg | 128/340 |
| 3,490,455 | 1/1970 | Illig | 128/303 R |
| 3,683,925 | 8/1972 | Frankel | 128/334 C |

FOREIGN PATENT DOCUMENTS

| | | | |
|---|---|---|---|
| 142571 | 10/1953 | Sweden | 128/334 R |
| 18231 | of 1897 | United Kingdom | 128/346 |

OTHER PUBLICATIONS

Stapling Techniques, General Surgery 2nd Edition, United States Surgical Corporation, pp. 22–23 (6/1980).
Sklar Surgical Instruments Catalog (1973) p. 59.

*Primary Examiner*—Michael H. Thaler
*Attorney, Agent, or Firm*—Frost & Jacobs

[57] ABSTRACT

A device for emplacing a purse-string suture in a severed end of a colon or other tubular structure. The device is generally barrette-like and has teeth on the upper and lower jaws which are mutually opposed so as to compress the tissue placed between the jaws and to permit tissue to bulge out into spaces between the respective teeth. Each jaw is provided with a needle guide or track through which a straight needle and suture may be passed and in passing through the needle track it will pass through the bulged out portions of the tissue. To emplace a purse-string suture, the needle is passed through one of the jaws in one direction and then looped around and passed through the other jaw in the opposite direction. A cutting guide is provided for severing excess tissue to provide a suitable cuff.

12 Claims, 14 Drawing Figures

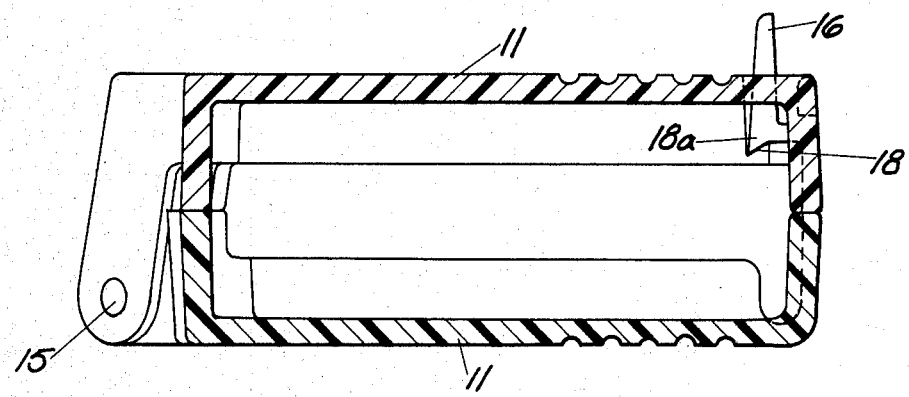
Fig. 3
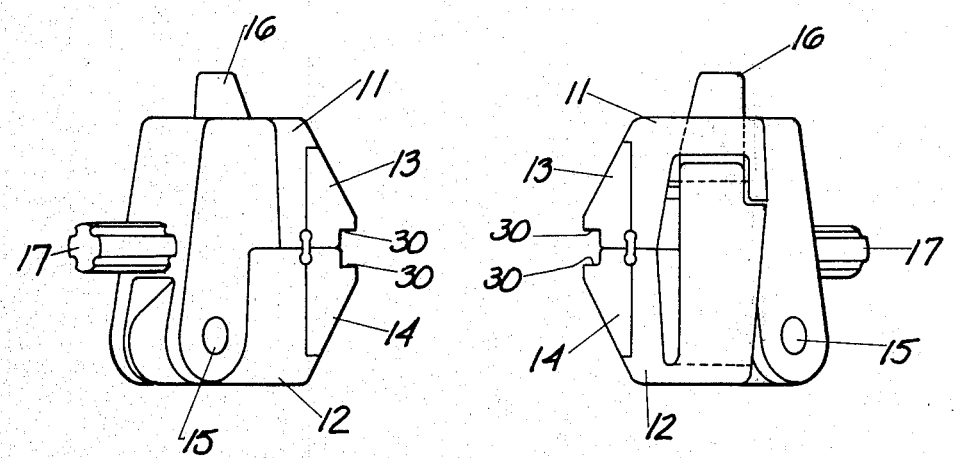
Fig. 4
Fig. 5

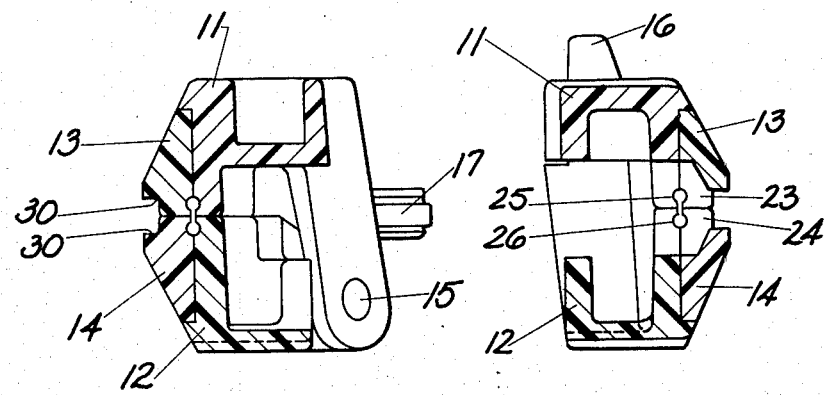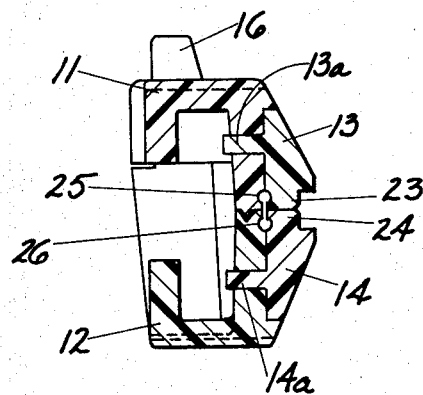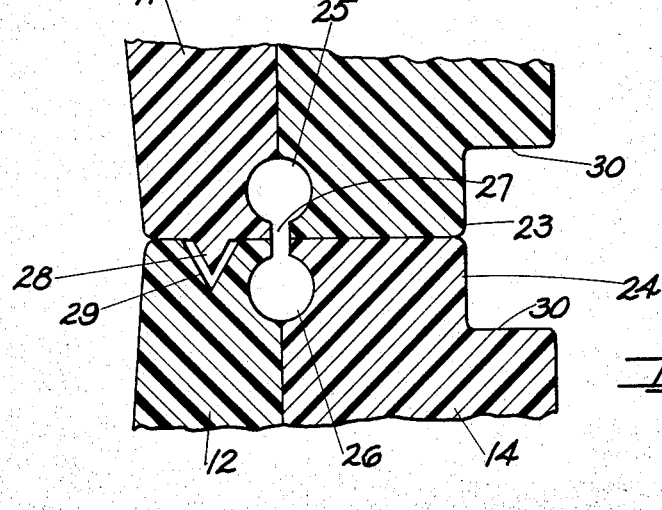

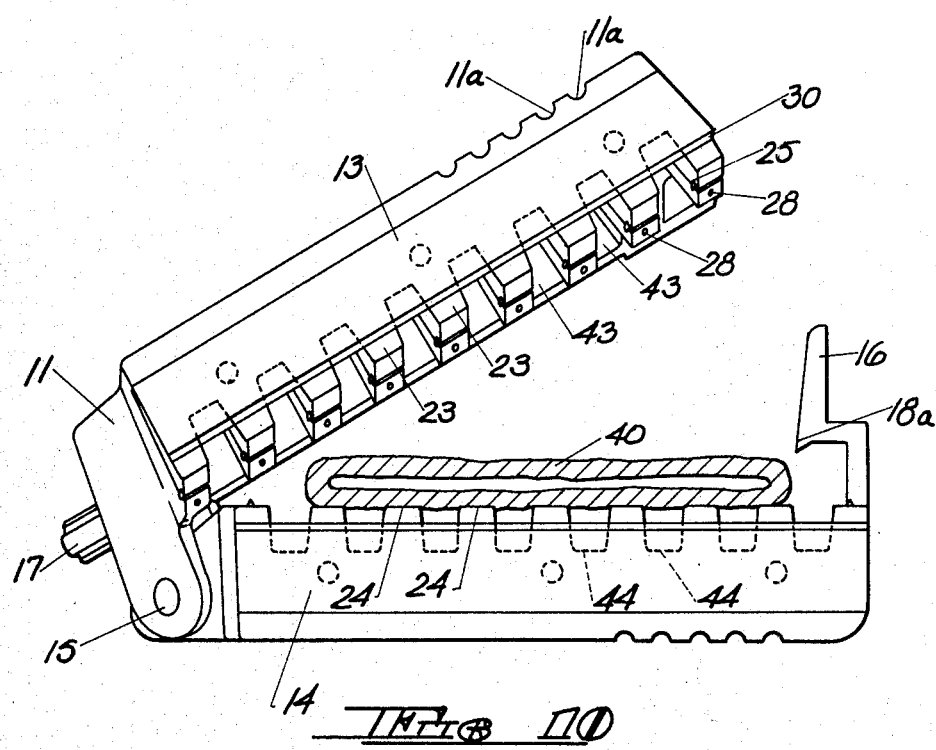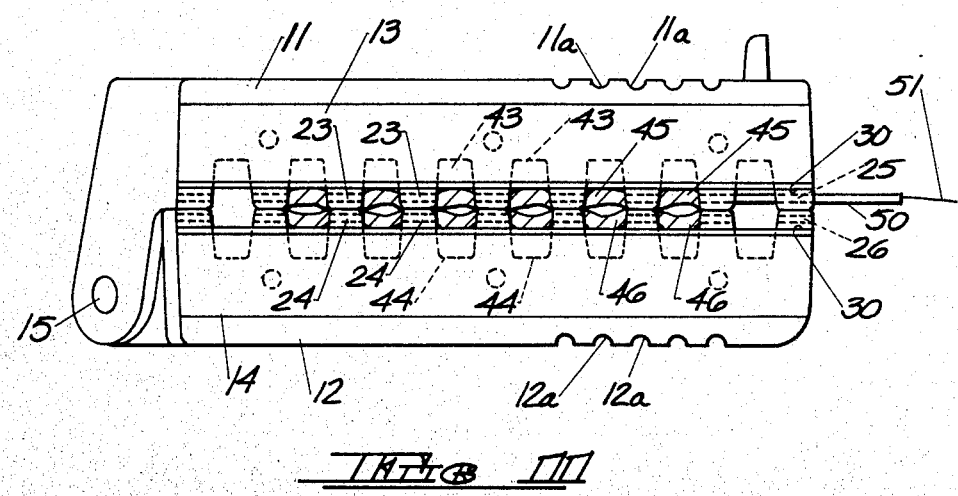

PURSE-STRINGER

CROSS REFERENCE TO RELATED APPLICATIONS

This application is related to an application in the name of Carl T. Becht, Ser. No. 890,262, filed Mar. 27, 1978, now U.S. Pat. No. 4,207,898, and an application in the name of Robert G. Rothfuss, Ser. No. 06/124,954, filed Feb. 26, 1980, now U.S. Pat. No. 4,319,576, both relating to an intraluminal anastomosis device for use in surgery.

BACKGROUND OF THE INVENTION

In recent years the use of staples instead of sutures in surgical procedures has become more and more conventional. The use of staples saves a good deal of time over the use of sutures and therefore means that the patient has to spend less time under anesthesia and this is of great benefit to the patient.

Stapling instruments have also begun to be used in many intestinal procedures from the esophagus to the rectum. Here again a great deal of time is saved and some of the difficult procedures are made much simpler.

The above referenced applications describe and claim intraluminal anastomosis devices for use in various procedures such as, for example, where a section of colon has been excised and it is necessary to rejoin the remaining portion of the colon. The instruments of the above applications connect the two portions of the colon by means of a double row of staples.

In order to use the instrument above mentioned, each portion of the colon must be provided with a purse-string suture. This is usually done by hand with an appropriate suture and needle. This procedure is difficult and time-consuming and gives rise to a number of problems. If the stitches are too far apart, the infolded tissue can extend beyond the diameter of the anvil of the instrument. In such situation, a leak will develop after the tissues are stapled and excised from the instrument. Furthermore, if too large a cuff or margin of tissue is left beyond the purse-string suture line, there may be more tissue inside the instrument that it can accommodate. This makes it impossible to close the instrument to the proper gap setting for stapling and then the instrument may either not be operable or the staples may be formed too loosely or not at all. Any of the foregoing situations can cause serious problems and complications.

There is on the market a permanent reusable instrument marketed by U.S. Surgical Corporation for facilitating the placement of a purse-string suture in round hollow organs. This instrument is essentially a hemostat having two angulated bars centrally attached with interdigitating teeth. In the U.S. Surgical device, each of the bars has a through-hole through which a straight needle with a suture can pass. The intestinal tissue is inserted between the two bars with the interdigitating teeth and is clamped by those teeth into a convoluted configuration. As the needle passes through the hole in the upper bar it also passes through the tissue that has been forced between the teeth by the teeth on the lower bar, and vice versa.

This device is subject to a number of shortcomings. It is a common occurrence for the needle to pass through both sides of the flattened intestinal tissue, thus sewing the opposite sides together instead of putting in a purse-string stitch. Additionally, the tissue which is clamped can readily slide normal to the bars and this makes it very difficult to cut to provide a minimum even margin along the edge of the bars. Since this device is a permanent-type instrument, it must be carefully maintained and it must be sterilized for each procedure.

The purse-stringer described herein overcomes all of the above-mentioned shortcomings and objections by virtue of design features which will be described and also by being designed for pre-sterile disposable one-time use.

BRIEF SUMMARY OF THE INVENTION

The device of the present invention comprises a pair of jaws hinged together at one end and provided with latching means at the other end. The jaws are provided with teeth but the teeth are mating teeth rather than interdigitating teeth, i.e. each tooth of the upper jaw contacts a tooth of the lower jaw. Thus, when a section of colon or the like is inserted between the jaws and clamped, the portions between the abutting teeth are flattened and the portions between the teeth bulge out into the spaces between the teeth.

In each jaw there is a through-hole respectively above and below the line of contact of the teeth so that a straight needle and suture can be passed through the through-hole in the upper jaw and then looped and passed back through the through-hole in the lower jaw. The needle and suture will pass through those portions of the colon section which have bulged up and down, respectively, between the teeth so that when the device is unlatched and removed, a purse-string suture is found to be properly in place. The device includes cutting guides spaced at an appropriate distance from the purse-string suture so that a cuff of the desired length is produced. In order to facilitate the cutting, the respective jaws are provided with opposed projections and depressions which engage the section of colon which is clamped and prevents slippage during cutting.

BRIEF DESCRIPTION OF THE FIGURES OF THE DRAWING

FIG. 3 is a cross sectional view taken on the line 3—3 of FIG. 2.

FIG. 4 is an end view as seen from the hinged end.

FIG. 5 is an end view as seen from the latch end of the device.

FIG. 6 is a cross sectional view taken on the line 6—6 of FIG. 1.

FIG. 7 is a cross sectional view taken on the line 7—7 of FIG. 1.

FIG. 8 is a cross sectional view taken on the line 8—8 of FIG. 1.

FIG. 9 is a greatly enlarged view similar to FIG. 8, showing the details of the through-holes and the communicating passage between them and the projections and depressions for preventing slippage.

FIG. 10 is a front elevational view of the device open with a section of intestine positioned for clamping.

FIG. 11 is a view similar to FIG. 10 showing the device closed and showing the needle and suture being inserted.

DETAILED DESCRIPTION

Figure 1:
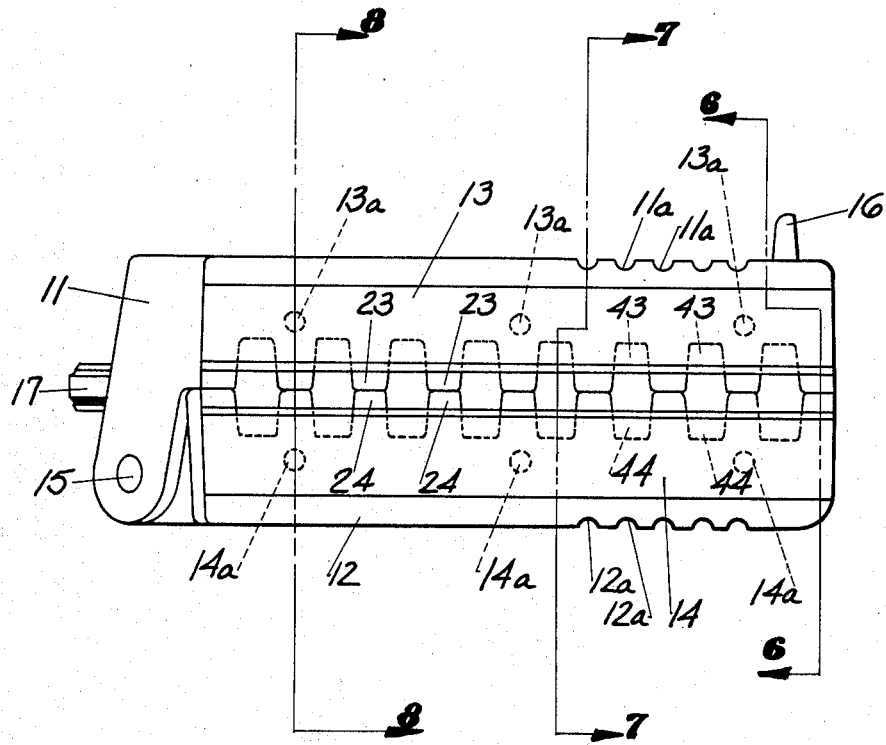
FIG. 1 is a front elevation of the device.
Figure 2:
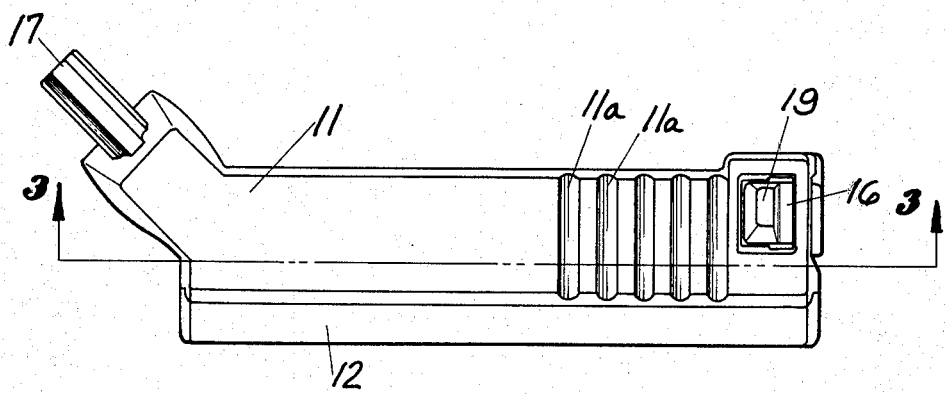
FIG. 2 is a plan view of the same.

By reference to FIG. 1, it will be seen that the device consists of an upper body 11 and a lower body 12 which are hinged together by means of a pin 15. Secured to the upper body 11 is the upper jaw 13 and similarly secured to the lower body 12 is the lower jaw 14. The upper jaw 13 is secured to the upper body 11 by means of the studs 13a which are pressed into the body 11 and the lower jaw 14 is similarly secured to the lower body 12 by the studs 14a. This is best seen in FIG. 8. It will be understood that the body and jaw in each case may be made integral. The bodies and jaws, whether separate or integral, are preferably constructed of a plastic material which is suitable for the design which must be molded and which is suitable for a surgical environment, that is, it must be capable of being sterilized by any of the standard methods such as autoclave, ethylene oxide, irradiation, etc. The parts will preferably be molded and assembled by press-fitting or with adhesives or with sonic welding.

The upper jaw is provided with a series of teeth 23 and the lower jaw is similarly provided with a series of teeth 24. It should be noted that these teeth are mutually opposed rather than interdigitating as in the U.S. Surgical device. The teeth are spaced apart preferably by about the same width as the width of the teeth to provide the spaces 43 and 44, respectively. The upper body 11 is provided with an angular portion which includes a hinge with hinge pin 15 and a stud 17 for gripping by means of a hemostat or similar instrument. Ridges 11a and 12a may be provided in the upper and lower body to provide a non-slip finger-grip for clamping the device shut.

It will be observed that the upper body has a latch aperture 19 and that the lower body carries a latch member 16. The upper body has a latching notch 18 (FIG. 3) and the latch member 16 has a latching nose 18a adapted to engage with the notch or ledge 18. The latch 16 as perhaps best seen in FIG. 10 is sufficiently thin that it can be bent in a clockwise direction for unlatching and can yield in a clockwise direction so as to snap back counter-clockwise over the ledge 18.

The upper jaw is provided with the through-hole 25 and the lower jaw is provided with a similar through-hole 26. These through-holes are best seen in the greatly enlarged cross sectional view of FIG. 9. It will be observed that there is a communicating passage 27 between the two through-holes provided by a passage from the respective through-holes 25 and 26 to the engaging surfaces of the respective teeth 23 and 24. The purpose of the passage 27 is to permit the suture to be removed from the device when the clamp is opened since the suture will be passing through the through-hole 25 and back through the through-hole 26 and means must be provided to permit the suture to be removed from these holes.

In FIG. 9 there is also shown more clearly one of the projections 28 and corresponding recesses 29. The projections 28 may be conical and come to a relatively sharp point and the depressions 29 may be correspondingly conical. By reference to FIG. 10, it is clear that a conical projection 28 is provided for each tooth 23. The series of projections 28 will secure the tissue 40 to prevent its sliding during severing.

FIG. 11 shows how, when the device is clamped on a section of colon or other tubular structure 40, portions thereof between the opposed teeth 23 and 24 bulge out into the spaces 43 and 44 as indicated at 45 and 46. By reference to FIG. 11 the through-holes 25 and 26 are seen to be respectively above and below the contact line of the teeth 23 and 24 so that they permit the needle 50 and suture 51 to pass through the portions 45, bulging upward into the spaces 43 and after looping around and passing through the through-hole 26 the suture passes through the portions 46 which bulge out into the spaces 44. When this operation is completed, the latch 16 is pressed in a clockwise direction as seen in FIGS. 1 and 3, to release the member 18a from the notch 18 and permit the jaws to open. The purse-string can then pass through the passage 27 and the tissue with the purse-string in place is removed.

Figure 12:
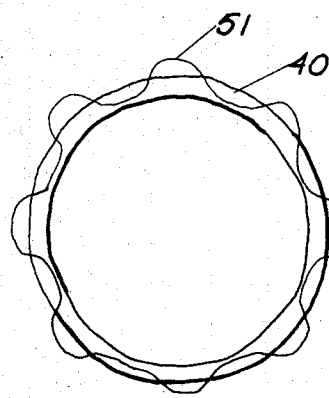
FIG. 12 is an end view of a section of intestine or the like with the purse-string suture in place.
Figure 13:
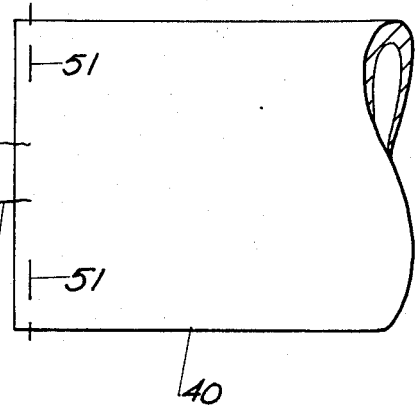
FIG. 13 is a side view of the same.

FIG. 12 shows an end view of a section of colon or other tubular structure showing the purse-string 51 in place and FIG. 13 shows a side view thereof.

Figure 14:
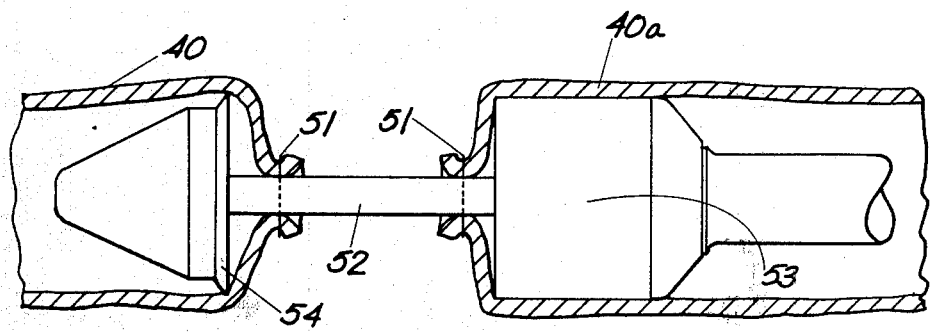
FIG. 14 is a somewhat schematic view showing how the purse-string sutures are applied to an intraluminal stapling instrument.

In an intraluminal anastomosis device there is an anvil portion and a cartridge portion. The anvil portion is indicated in FIG. 14 at 54 and the cartridge portion at 53. The adjusting rod is indicated at 52. FIG. 14 shows how the sections of colon or other tubular structure 40 and 40a are secured around the adjusting rod 52 by means of the purse-string sutures 51.

In several of the Figures, the cutting guides have been indicated at 30. After the device of the present invention has been used to emplace the purse-string suture, a scalpel can be run along either of the guides 30 to sever excess tissue and leave a cuff of designed length. This is simply based upon the distance between the suture lines 25 and 26 and the cutting guides 30.

It will be understood that numerous modifications may be made without departing from the spirit of the invention and for this reason no limitations which are not expressly set forth in the claims should be assumed or implied.

What is claimed is:

1. An instrument to facilitate the emplacement of a purse-string suture in a tubular structure, comprising a barrette-like structure having upper and lower jaws hinged together at one end, said jaws having longitudinally spaced clamping teeth with each of the teeth on said upper jaw being directly opposed to a corresponding tooth on said lower jaw whereby when a tubular structure is clamped between said jaws, the portions thereof between the pairs of opposing clamping teeth bulge out into the spaces between the teeth, a needle track extending longitudinally in each of said jaws disposed respectively above and below the clamping line of said teeth, whereby a needle and suture, in passing through the track of one of said jaws passes the suture through the portions of said tubular structure bulging into the spaces between the teeth on said one of said jaws, and in passing back through the track on the other of said jaws passes the suture through the portions of said tubular structure bulging into the spaces between the teeth on said other jaw, the tracks in the respective jaws communicating with each other, so that, when said jaws are unlatched and opened, said tubular structure, with the purse-string suture in place, may be removed from the instrument.

2. The instrument of claim 1 wherein the width of the spaces between the respective pairs of upper and lower teeth is about the same as the width of said teeth.

3. The instrument of claim 1 wherein one of said jaws is provided with a stud for engagement by a hemostat or the like.

4. The instrument of claim 1 wherein each of said jaws is provided with a cutting guide spaced from said needle track by a distance to provide a suitable cuff when excess tissue is cut off by means of a scalpel.

5. The instrument of claim 4 wherein one of said jaws is provided with a number of projections, and the other of said jaws is provided with a corresponding number of mating depressions, the projections and depressions cooperating to hold the clamped tissue and prevent its sliding when excess tissue is severed by means of a scalpel.

6. The instrument of claim 5 wherein said projections are conical, and said depressions conform to the conical shape of said projections.

7. The instrument of claim 1 wherein said jaws are provided with cooperating latching means.

8. The instrument of claim 8 wherein said upper jaw is provided with a latch aperture and a latch seat, and wherein said lower jaw is provided with a latch member biased to engagement with said latch seat, said latch member having a releasing portion extending through said aperture for engagement by the surgeon's finger or with suitable instrument.

9. The instrument of claim 8, being of plastic material, said latch member being integral with said lower jaw and being resilient, so as to snap into engagement with said latch seat, and being releasable by a finger actuation of said releasing portion.

10. The instrument of claim 1 molded of a plastic material capable of sterilization by standard methods, and thus being pre-sterilizable for disposable one-time use.

11. The instrument of claim 1, wherein the axis of hinging is at an angle to the axis of said jaws, and wherein one of said jaws is provided with a stud normal to said hinging axis for engagement by a hemostat or the like at an angle convenient for the surgeon.

12. The instrument of claim 1 wherein the position of the needle tracks in said jaws are so disposed above and below with respect to the clamping line of said teeth as to insure proper placement of the purse-string suture in said tubular structure.

* * * * *